US006143879A

United States Patent [19]
Que, Jr. et al.

[11] Patent Number: 6,143,879
[45] Date of Patent: Nov. 7, 2000

[54] NUCLEOTIDE CLEAVING AGENTS AND METHOD

[75] Inventors: Lawrence Que, Jr., Roseville; Richard S. Hanson, Falcon Heights; Leah M. T. Schnaith, Redwing, all of Minn.

[73] Assignee: Regents of the University of Minnesota, Minneapolis, Minn.

[21] Appl. No.: 09/123,848

[22] Filed: Jul. 28, 1998

Related U.S. Application Data

[63] Continuation-in-part of application No. 08/614,915, Mar. 13, 1996, abandoned, which is a continuation of application No. 08/181,851, Jan. 14, 1994, abandoned.

[51] Int. Cl.⁷ .......................... C07H 21/00; C07H 21/02; C07H 21/04
[52] U.S. Cl. ...................... 536/23.1; 536/24.3; 536/25.3; 536/24
[58] Field of Search ................................ 536/23.1, 25.3, 536/24.3, 124

[56] References Cited

U.S. PATENT DOCUMENTS

| | | | |
|---|---|---|---|
| 4,665,184 | 5/1987 | Dervan et al. | 546/109 |
| 4,795,700 | 1/1989 | Dervan et al. | 435/5 |
| 4,942,227 | 7/1990 | Dervan et al. | 536/23.1 |

FOREIGN PATENT DOCUMENTS 9119730  12/1991  WIPO.

OTHER PUBLICATIONS

Heppel et al., "A Study of the Substrate Specificity and Other Properties of the Alkaline Phosphatase of *Escherichia coli*," *Journal of Biological Chemistry*, 237(3), 841–846 (Mar. 1962).

Dreyer et al., "Sequence–Specific Cleavage of Single Stranded DNA: Oligonucleotide–EDTA•Fe(II)," *Proc. National Academy Sciences USA*, 82, 968–972 (1985).

Chu et al., "Nonenzymatic Sequence Specific Cleavage of Single Stranded DNA," *Proc. National Academy Sciences USA*, 82, 963–967 (1985).

Francois et al.(I), "Nuclëases Artificielles: Coupures Spëcifiques de la Double Hëlice d'ADN par des Oligonuclëotides liës au Complexe Cuivre–Phënanthroline," *Compte Rend. Acad. Science Paris*, 307, Ser. III, 849–854 (1988).

Francois et al.(II, "Periodic Cleavage of Poly(dA) by Oligothymidylates Covalently Linked to the 1,10–Phenanthroline–Copper Complex," *Biochemistry*, 27(7), 2272–2276 (1988).

Hëlëne et al., "Sequence Specific Artificial Endonucleases," *Trends in Biotechnology*, 7, 310–315 (1989).

Doan et al., "Sequence–Targeted Chemical Modifications of Nucleic Acids by Complementary Oligonucleotides Covalently Linked to Porphyrins," *Nucleic Acids Research*, 15(21), 8643–8659 (1987).

Sun et al., "Sequence–Targeted Cleavage of Nucleic Acids by Oligo–α–thymidylate–Phenanthorline Conjugates: Parallel and Antiparallel Double Helices Are Formed with DNA and RNA, Respectively," *Biochemistry*, 27(16), 6039–6045 (1988).

Biodet–Forget et al., "Site–Specific Cleavage of SIngle–Stranded and Double–Stranded DNA Serquences by Oligodeoxyribonucleotides Covalently Linked to an Intercalating Agent and an EDTA–Fe Chelate," *Gene*, 72, 361–371 (1988).

Hëlëne et al., "Control of Gene Expression by Oligodeoxynucleotides Covalently Linked to Intercalating Agents and Nucleic Acid–Cleaving Reagents,", Ch. 7 in *Oligodeoxynucloeotides. Antisense Inhibitors of Gene Expression*, J. S. Cohen ed., CRC Press, Boca Raton, FL, 1989, pp. 137–172.

Schnaith et al. ,"Double–Stranded Cleavage of pBR322 by a Diiron Complex Via a 'Hydrolytic' Mechanism," *Proc. National Academy Sciences USA*, 91, 569–573 (1994).

Adams et al., "Hindered Dialkylamino Nucleoside Phosphite Reagents in the Synthesis of Two DNA 51–Mers," *J. Am. Chem. Soc.*, 105, 661–663 (1983).

Ausubel et al., *Current Protocols in Molecular Biology*, Greene Publishing Associates and Wiley Interscience; NY; pp. 3.4.1–3.4.9 (1987).

Barton et al., "Site–Specific cleavage of left–handed DNA in pBR322 by Λ–tris (diphenylphenanthroline) cobalt (III)," *Proc. Natl. Acad. Sci. USA*, 82, 6460–6464 (1985). (Oct., 1985).

Basile et al., "Metal–Activated Hydrolytic Cleavage of DNA," *J. Am. Chem. Soc.*, 109, 7550–7551 (1987).

Beaucage et al., "Deoxynucleoside Phosphoramidites—A New Class of Key Intermediates for Deoxypolynucleotide Synthesis," *Tetrahedron Letters*, 22, 1859–1862 (1981). (issue No. 20).

Birnboim et al., "A rapid alkaline extraction procedure for screening recombinant plasmid DNA," *Nucl. Acids. Res.*, 7, 1513–1523 (1979). (Issue No. 6).

Bloomfield, "Molecular Biophysics Training Program," Abstract of Department of Health and Human Services Grant No. GM–08277 (1988).

Branum et al., "Dinuclear Lanthanide Complexes as Hydrolytic DNA Cleavage Agents," abstract and poster from American Chem. Society, Division of Inorganic Chemistry, 212th National Meeting, Orlando, FL, Aug. 25–29, 1996.

(List continued on next page.)

*Primary Examiner*—Paul J. Killos
*Assistant Examiner*—L. E. Crane
*Attorney, Agent, or Firm*—Mueting, Raasch & Gebhardt, P.A.

[57] ABSTRACT

The present invention provides a unique series of nucleotide cleaving agents and a method for cleaving a nucleotide sequence, whether single-stranded or double-stranded DNA or RNA, using and a cationic metal complex having at least one polydentate ligand to cleave the nucleotide sequence phosphate backbone to yield a hydroxyl end and a phosphate end.

28 Claims, 5 Drawing Sheets

OTHER PUBLICATIONS

Brennan et al., "Models for Diiron–Oxo Proteins: The Peroxide Adduct of $Fe_2$ (HPTB) (OH) $NO_3)_4$," *Inorg. Chem.*, 30, 1937–1943 (1991). (Issue No. 8).

Burke et al., "Cloning of Large Segments of Exogenous DNA into Yeast by Means of Artificial Chromosome Vectors," *Science*, 236, 806–812 (1987).

Chen et al., "DNA Modification: Intrinsic Selectivity of Nickel (II) Complexes," *J. Am. Chem. Soc.*, 113, 5884–5886 (1991). (Issue No. 15).

Chin et al., "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111, 4103–4105 (1989). (Issue No. 11).

Coleman et al., "Alkaline Phosphatase, Solution Structure, and Mechanism," *Adv. Enzymol.*, 55, 381–452 (1983).

DeRosch et al., "Hydrolysis of Phosphodiesters with Ni (II), Cu (II), Pd (II), and Pt (II) Complexes," *Inorg. Chem.*, 29, 2409–2416 (1990). (Issue No. 13).

Dervan, "Design of Sequence–Specific DNA–Binding Molecules," *Science*, 232, 464–471 (1986). (Apr. 25, 1986).

Dong et al., "Dioxygen Binding to Diferrous Centers. Models for Diiron–Oxo Proteins," *J. Am. Chem. Soc.*, 115, 1851–1859 (1993). (Issue No. 5).

Dorman et al., "Synthesis of Oligodeoxynucleotides and Oligodeoxynucleotide Analogs using Phosphoramidite Intermediates," *Tetrahedron*, 40, 95–102 (1984). Iss. No. 1).

Ettner et al., "Enhanced Site–Specific Cleavage of the Tetracycline Repressor by Tetracycline Complexed with Iron," *J. Am. Chem. Soc.*, 115, 2546–2548 (1993). (Iss. No. 6).

Hanahan, "Techniques for Transformation of *E. coli*," in *DNA Cloning: A Practical Approach*, 1, pp. 109–136 (1985).

Hanson, "Genetics of Bacteria that Utilize One–Carbon Compounds," Abstract of Department of Energy Grant No. DE–AC02–82ER 12029 (1987).

Hendry et al., "Metal Ion Promoted Reactions of Phosphate Derivatives," in *Progress in Inorganic Chemistry: Bioinorganic Chemistry*, 38, S.J. Lippard (Ed.); John Wiley & Sons, Inc.: New York; pp. 201–258 (1990).

Khorana, "Total Synthesis of a Gene," *Science*, 203, 614–625 (Feb. 1979).

Kimball et al., "Sequence–Specific Cleavage of DNA via Nucleophilic Attack of Hydrogen Peroxide, Assisted by Flp Recombinase," *Biochemistry*, 32, 4698–4701 (1993). (Issue No. 18).

Langer et al., "Enzymatic synthesis of biotin–labeled polynucleotides: Novel nucleic acid affinity probes," *Proc. Nat. Acad. Sci.*, 78, 6633–6637 (Nov. 1981). (Issue No. 11).

Lilley, "The inverted repeat as a recognizable structural feature in supercoiled DNA molecules," *Proc. Natl. Acad. Sci. USA*, 77, 6468–6472 (1980). (Nov. '80).

Maniatis et al., "Gel Electrophoresis," in *Molecular Cloning. A Laboratory Manual;* Cold Spring Harbor Laboratory: Cold Spring Harbor, NY; pp. 149–172 (1982).

Matteucci et al., "Synthesis of Deoxyligonucleotides on a Polymer Support," *J. Am. Chem. Soc.*, 103, 3185–3191 (1981). (Issue No. 11).

Maxam et al., "Sequencing End–Labeled DNA with Base–Specific Chemical Cleavages," *Methods in Enzymology*, 65, 499–560 (1980).

Meunier, "Metallaporphyrins as Versatile Catalysts for Oxidation Reactions and Oxidative DNA Cleavage," *Chem. Rev.*, 92, 1411–1456 (1992). (Issue No. 6).

Modak et al., "Toward Chemical Ribonucleases. 2. Synthesis and Characterization of Nucleoside–Bipyridin Conjugates. Hydrolytic Cleavage of RNA by Their Copper (II) Complexes," *J. Am. Chem. Soc.*, 113, 283–291 (1991). (Iss. No.

Morrow et al., "Efficient Catalytic Cleavage of RNA by Lanthanide (III) Macrocyclic Complexes: Toward Synthetic Nucleases for in Vivo Applications," *J. Am. Chem.*, 114, 1903–1905 (1992).

Murray et al., "Molecular Cloning of the DNA Ligase Gene from Bacteriophage T4," *J. Mol. Biol.*, 132, 493–505 (1979).

Nishida et al., "Synthesis and Reactivities of Binuclear Iron (II) Complexes with Ligands Composed of Two Tridentate Chelating Groups," *Inorganica Chimica Acta*, 96, 115–119 (1984).

Nishida et al., "DNA Cleavage by Binuclear Iron (III)—Peroxide Adducts," *Inorg. Chim. Acta*, 163, 9–10 (1989).

Povrik et al., "Competition between Anaerobic Covalent Linkage of Neocarzinostatin Chromophore to Deoxyribose in DNA and Oxygen–Dependent Strand Breakage and Base Release," *Biochemistry*, 23, 6304–6311 (1984).(Iss. No. 26).

Prizey, "Raney Nickel" in *Synthetic Reagents*, vol. II; Halsted Press: New York; pp. 175–311 (1974).

Pyle et al., "Probing Nucleic Acids with Transition Metal Complexes," *Prog. Inorg. Chem.*, 38, 413–475 (1990).

Pyle et al., "Shape–Selective Targeting of DNA by (Phenanthrenequinone diimine) rhodium (III) Photocleaving Agents," *J. Am. Chem. Soc.*, 111, 4520–4522 (1989). (Iss. No 1.

Que, Jr., "Synthetic approaches for Modeling Metal–Oxo Proteins," Abstract of National Institute of Health Grant No. GM–38767–07 (1986).

Rabow et al., "Identification and Quantitation of the Lesion Accompanying Base Release in Bleomycin–Mediated DNA Degradation," *J. Am. Chem. Soc.*, 112, 3203–3208 (1990). (Issue No. 8).

Rabow et al., "Identification of the Source of Oxygen in the Alkaline–Labile Product Accompanying Cytosine Release during Bleomycin–Mediated Oxidative Degradation of d(CGCGCG)," *J. Am. Chem. Soc.*, 112, 3203–3208 (1990). (Iss. No. 8).

Rana et al., "Transfer of oxygen from an artificial protease to peptide carbon during proteolysis," *Proc. Natl. Acad. Sci. USA*, 88, 10578–10582 (1991).(Dec. '91).

Reid et al., "*E. Coli* Alkaline Phosphatase" in *The Enzymes;* P.D. Boyer (Ed.); Academic Press: New York; pp. 373–415 (1971).

Sausville et al., "Properties and Products of the Degradation of DNA by Bleomycin and Iron (II)," *Biochemistry*, 17, 2746–2754 (1978). (Issue No. 14).

Schnaith, "Cleavage of Nucleic Acids by Activated Diiron Complexes," Ph.D. Thesis submitted to the University of Minnesota (Sep. 1994).

Schnaith et al., "Preferential Hydrolysis of PBR322 Plasmid by Diiron Complexes," Abstract and poster presented at ICBIC (International Conference on Bio. & Inorg. Chemistry), La Jolla, CA, Aug. 23–27, 1993, Poster No. H012. Abstract Published in *J. Inorganic Biochemistry*, 51, 525 (1993).

Sigman et al., "Targeted Chemical Nucleases," *Acct. Chem. Res.*, 26, 98–104 (1993). (Issue No. 3).

Spiro, "Phosphate Transfer and Its Activation by Metal Ions; Alkaline Phosphatase," in *Inorganic Biochemistry;* G.L. Eichorn (Ed.); American Elsevier: New York; pp. 549–581 (1973).

Stern et al., "Hydrolysis of RNA by Transition–Metal Complexes," *J. Am. Chem. Soc.,* 112, 5357–5359 (1990). (Issue No. 13).

Stubbe et al., "Mechanisms of Bleomycin–Induced DNA Degradation," *Chem. Rev.,* 87, 1107–1136 (1987). (Issue No. 5).

Sugiyama et al., "Structure of the Alkali–Labile Product Formed during Iron (II)–Bleomycin–Mediated DNA Strand Scission," *J. Am. Chem. Soc.,* 107, 4104–4105 (1985). (Issue No. 13).

Sugiyama et al., "Chemistry of the Alkali–Labile Lesion Formed for Iron (II) Bleomycin and d (CGCTT-TAAAGCG)," *Biochemistry,* 27, 58–67 (1988). (Iss. No. 1).

Sutcliffe, "pBR322 restriction map derived from the DNA sequence: accurate DNA size markers up to 4361 nucleotide pairs long," *Nucleic Acids Res.,* 5, 2721–2728, (Aug. 1978). (Issue No. 8).

Sutcliffe, "Complete Nucleotide Sequence of the *Escherichia coli* Plasmid pBR322," in *Cold Harbor Symp. Quant. Biol.,* 43, 77–90 (1978).

Takasaki et al., "Synergistic Effect between La(III) and Hydrogen Peroxide in Phosphate Diester Cleavage," *J. Am. Chem. Soc.,* 115, 9337–9338 (1993). (Iss. No. 20).

Tullius, "Physical Studies of Protein–DNA Complexes by Footprinting," *Annu. Rev. Biophys. Chem.,* 18, 213–237 (1989).

Uchida et al., "High Resolution footprinting of EcoRI and distamycin with $Rh(phi)_2(bpy)^{3+}$, a new photofootprinting reagent," *Nucleic Acids Res.,* 17, 10259–10279 (1989). (Issue No. 24).

Waravdeker et al., "A Sensitive Colorimetric Method for the Estimation of 2–Deoxy Sugars with the Use of the Malonaldehyde–Thiobarbituric Acid Reaction," *J. Biol. Chem.,* 234, 1945–1950 (1959). (Issue No. 8, Aug. 1959).

Weiss et al., "Enzymatic Breakage and Joining of Deoxyribonucleic Acid," *J. Biol., Chem.,* 243, 4543–4555 (1968). (Issue No. 17, Sep. 10, 1968).

Yoon et al., "High Turnover Rates in pH–Dependent Alkene Epoxidation Using NaOCl and Square–Planar Nickel (II) Catalysts," *J. Am. Chem. Soc.,* 112, 4568–4570 (1990). (Issue No. 11).

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CAGGCACCGT      10

NUCLEOTIDE CLEAVING AGENTS AND METHOD

CROSS-REFERENCE TO RELATED APPLICATIONS

This application is a Continuation-In-Part of U.S. application Ser. No. 08/614,915 (filed Mar. 13, 1996), which is a continuation of U.S. application Ser. No. 08/181,851 (filed Jan. 14, 1994) both now abandoned.

STATEMENT OF GOVERNMENT RIGHTS

The present invention was made with government support from the U.S. Department of Energy (Grant DE-FG02-88ER 13862) and the National Institutes of Health (Grants GM-38767 and GM-08277). The Government has certain rights in this invention.

BACKGROUND OF THE INVENTION

Nucleases are enzymes that cleave deoxyribonucleotides (DNA) or ribonucleotides (RNA) molecules, into smaller nucleotides fragments, e.g., oligonucleotides. Each enzyme recognizes a specific sequence of nucleotides, thereby cleaving the DNA or RNA at specific recognition sites. This sequence-specific cleavage is important in the production of smaller nucleotide fragments, gene isolation and sequencing, plasmid mapping, recombinant DNA manipulations, and the like. Unfortunately, however, the number of endonucleases is limited. Thus, chemically synthesized agents that cleave nucleotide sequences are important functional reagents for use in such molecular biology applications as well as in diagnostics and cancer therapy. They can be considered as artificial or synthetic nucleases.

Inorganic DNA cleaving reagents are one type of nucleotide cleaving agent of significant importance. The susceptibility of the ribose ring to oxidation has led to the use of a number of complexes that cleave DNA by oxidative mechanisms. Examples of such complexes include [Fe(EDTA)]⁻ (EDTA=ethylenediaminetetraacetic acid), [Cu(phen)]⁺ (phen=1,10-phenanthroline), and metalloporphyrins, which are activated by $H_2O_2$ or a reductant in the presence of $O_2$. Another example is the photo-activated $[Rh(phen)_3]^{2+}$ complexes. See, for example, Tullius, *Annu. Rev. Biophys. Chem.*, 18, 213–237 (1989); Dervan, *Science* 232, 464–471 (1986); Sigman et al., *Accts. Chem. Res.*, 26, 98–104 (1993); Meunier, *Chem. Rev.*, 92, 1411–1456 (1992); Pyle et al., *J. Am. Chem. Soc.*, 111, 4520–4522 (1989); Uchida et al., *Nucleic Acids Res.*, 17, 10259–10279 (1989). These cleaving agents are generally nonspecific. That is, they cleave DNA in a nonspecific manner, i.e., not at any one particular site or sequence.

The nonspecificity of the Fe(EDTA)-mediated cleavage has led to its use as a DNA footprinting reagent in identifying the binding locations of small molecules, such as proteins, antibiotics and other drugs, on DNA. That is, [Fe(EDTA)]⁻ is capable of being used to map the DNA binding location of small molecules because the bound molecule protects the DNA binding region from cleavage by the [Fe(EDTA)]⁻.

Sequence specificity can be incorporated into these cleaving agents by tethering DNA recognition elements to the metal complex, a design principle analogous to that used by the antitumor drug bleomycin. See, for example, Dervan, cited supra.,; Sigman et al., cited supra.; Dervan et al., U.S. Pat. No. 4,665,184; and Stubbe et al., *Chem. Rev.*, 87, 1107–1136 (1987). Bleomycin is a glycopeptide that binds to DNA and cleaves it at specific sites through the use of $Fe^{+2}$ and $O_2$ or $Fe^{3+}$ and $H_2O_2$. This principle involves the use of a DNA binding molecule to deliver a reactive metal complex to a specific sequence of nucleotides where cleavage occurs.

Whether site specific or not, the above-mentioned nucleotide cleaving agents operate oxidatively, thereby destroying a ribose ring to engender strand scission, i.e., cleavage. In this way the nucleotide sequence is not simply "cut" in such a way as to leave a 3' hydroxyl on one end and a 5' phosphate on the other, but the smaller pieces formed are effectively changed. This means the smaller pieces of DNA cannot be used in typical DNA cloning procedures, e.g., incorporation of a DNA fragment into a plasmid that can be amplified. Thus, the focus is shifting to the development of reagents that can cleave polynucleotides into fragments that can be readily cloned.

Hydrolytic reagents cleave polynucleotides through hydrolysis of the phosphate backbone as do restriction endonucleases in such a way as to leave a hydroxyl on one end and a phosphate on the other end. In this way the nucleotide sequence is simply "cut" into smaller pieces that can be used in typical cloning procedures. A number of metal ion complexes have been shown to hydrolyze phosphate esters as well as RNA with varying efficiencies; however, they are unable to hydrolyze the phosphate diester backbone of DNA. See, for example, Hendry et al., *Prog. Inorg. Chem.*, 38, 201–258 (1990); DeRosch et al., *Inorg. Chem.*, 29, 2409–2416 (1990); Modak et al., *J. Am. Chem. Soc.*, 113, 283–291 (1991); Morrow et al., *J. Am. Chem.*, 114, 1903–1905 (1992); Chin et al., *J. Am. Chem. Soc.*, 111, 4103–4105 (1989); and Stern et al., *J. Am. Chem. Soc.*, 112, 5357–5359(1990). The only reported metal-catalyzed DNA hydrolysis thus far is effected by $Cu^{+2}$, $Co^{+2}$, $Zn^{+2}$, $Cd^{+2}$, or $Pb^{+2}$ complexed to a polyamine ligand tethered to a DNA binding $[Ru(phen)_3]^{2+}$ derivative, which afforded nicked (single stranded break) pBR322 at 37° C. after 5–7 hours. Basile et al., *J. Am. Chem. Soc.*, 109, 7550–7551(1987).

Thus, what is needed are effective agents that can cleave both DNA and RNA, single-stranded or double-stranded, particularly in the phosphate backbone in a manner in which the nucleotide sequence is cut to leave a hydroxyl on one end and a phosphate on the other end. Furthermore, what is needed are cleaving agents capable of cleaving nucleotide sequences in this manner at specific recognition sites.

SUMMARY OF THE INVENTION

The present invention provides a new class of nucleotide cleaving agents and a method for cleaving a nucleotide sequence, whether single-stranded or double-stranded DNA or RNA. The method uses a cationic metal complex having at least one polydentate ligand and preferably a dioxygen source. The cationic metal complex optionally can be a nucleophilic peroxide-generating cationic metal complex, i.e., one that is capable of generating a nucleophilic peroxide in the presence of a dioxygen source such as $O_2$. The cationic metal complex is preferably a dinuclear metal complex with one or two polydentate ligands. More preferably, the cationic metal complex is a dinuclear metal complex having at least one ligand containing two tridentate chelating groups linked by a polyatomic chain. The cleavage typically occurs in the sugar phosphate backbone of the nucleotide sequence to form a hydroxyl end and a phosphate end, although this may not be a necessary requirement of all embodiments of the invention.

The metal complex is preferably a dinuclear metal complex of a Lewis acidic metal. More preferably, the metal is a Group IIIA, IB, VB, VIIB, VIIIB, or a lanthanide series metal. Preferably, the metal complex contains at least one ligand, and typically one or two ligands, represented by the formula $(R^1)(R^2)N—R^3—N(R^4)(R^5)$ wherein: each of $R^1$, $R^2$, $R^4$, and $R^5$ is independently a Lewis basic group; and $R^3$ is a substituted or unsubstituted aliphatic or aromatic group, preferably with at least a 3-carbon chain. An example of a ligand of this type is N,N,N',N'-tetrakis(2-pyridylmethyl)-2-hydroxy-1,3-diaminopropane. Specific examples of such complexes are $Fe_2(HPTB)(OH)(NO_3)_4$, $Fe_2(HPTP)(OH)(NO_3)_4$, and $[Fe_2(HPTP)(OBz)](BPh_4)_2$.

The following abbreviations are used herein: bp=base pair; DMSO=dimethylsulfoxide; DTT=dithiothreitol; EtdBr=ethidium bromide; HPTB=N,N,N',N'-tetrakis(2-benzimidazolylmethyl)-2-hydroxy-1,3-diaminopropane; HPTP=N,N,N',N'-tetrakis(2-pyridylmethyl)-2-hydroxy-1,3-diaminopropane; HPTA=2-hydroxypropane-1,3-diamine tetraacetic acid; MMPP=magnesium monoperoxyphthalate; oxone=potassium peroxymonosulfate; phen=1,10-phenanthroline; EDTA=ethylenediaminetetraacetic acid; LB=Luria-Bertani.

DETAILED DESCRIPTION OF THE INVENTION

Figure 1:
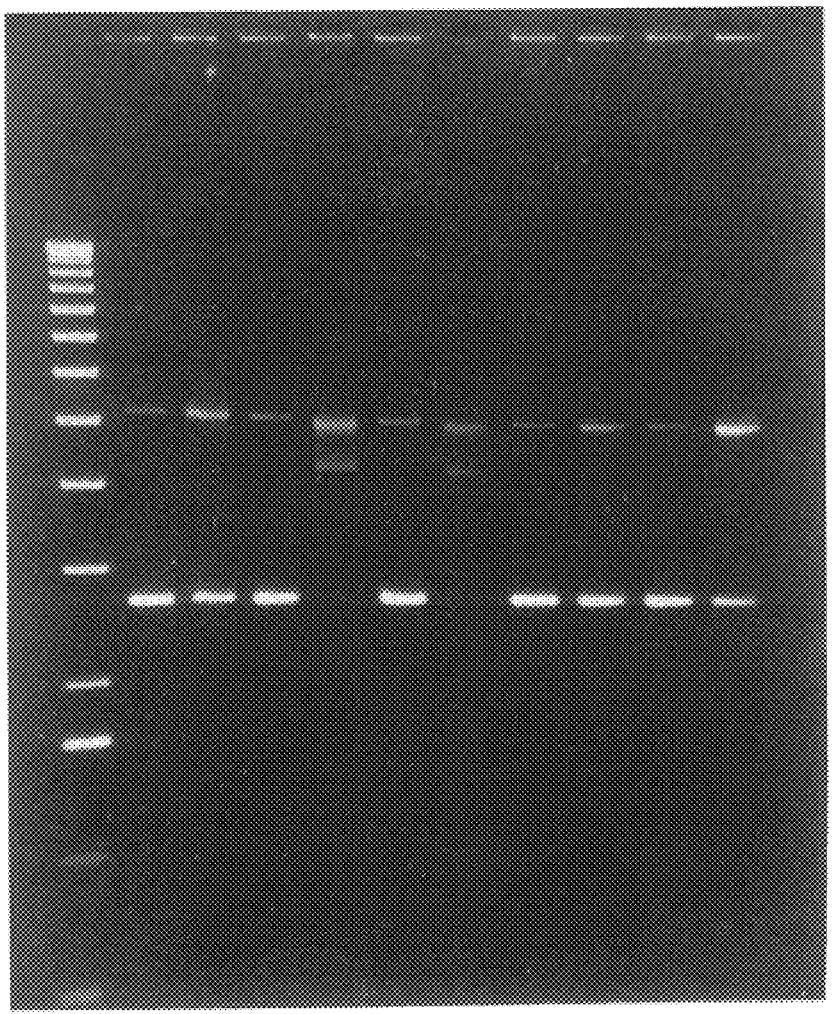
FIG. 1: pBR322 Cleavage Experiments. Lane 1=1 kilobase ladder. Lane 2=untreated pBR322. Lane 3=pBR322+10 $\mu$M $Fe_2(HPTB)(OH)(NO_3)_4$. Lane 4=pBR322+60 $\mu$M $H_2O_2$. Lane 5=pBR322, 10 $\mu$M $Fe_2(HPTB)(OH)(NO_3)_4$, and 60 $\mu$M $H_2O_2$. Lane 6=pBR322+60 $\mu$M ascorbate. Lane 7=pBR322, 10 $\mu$M $Fe_2(HPTB)(OH)(NO_3)_4$, and 60 $\mu$M ascorbate. Lane 8=pBR322+60 $\mu$M MMPP. Lane 9=pBR322, 10 $\mu$M $Fe_2(HPTB)(OH)(NO_3)_4$, and 60 $\mu$M MMPP. Lane 10=pBR322+60 $\mu$M $KHSO_5$. Lane 11=pBR322, 60 $\mu$M $KHSO_5$, and 10 $\mu$M $Fe_2(HPTB)(OH)(NO_3)_4$. Reactions were conducted at room temperature in the atmosphere at pH=8.0 and occurred upon mixing. Glycerol and bromophenol blue dye were added to the samples, and the solutions were immediately loaded onto a 1.0% agarose gel in a 40 mM Tris•acetate, 1 mM EDTA buffer which was run at 70 volts for 5 hours.
Figure 2:
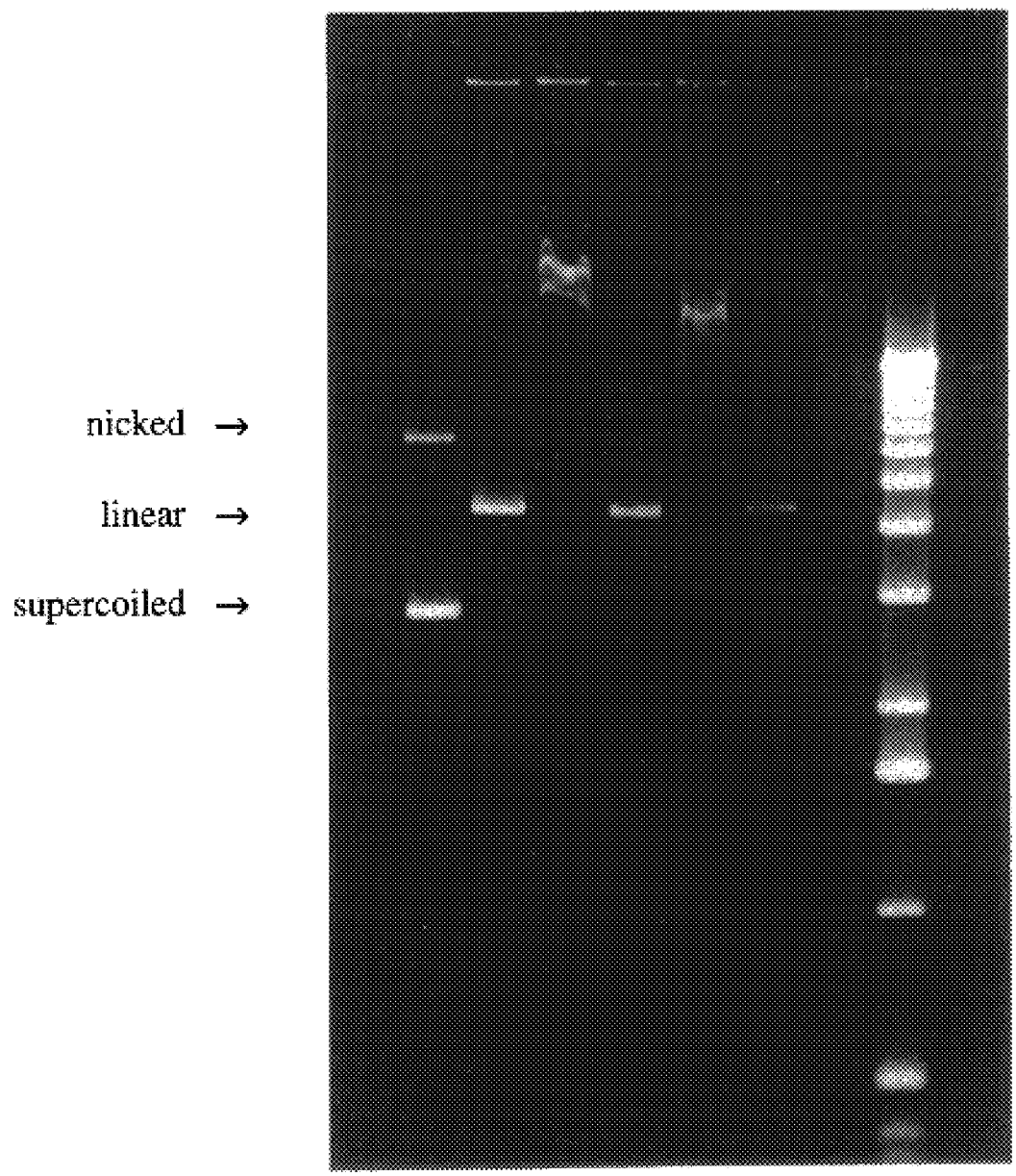
FIG. 2: Ligation of Linearized pBR322. Lane 1 contains supercoiled (lower band) and nicked pBR322. Lanes 2 and 3 compare Hind III linearized plasmid without and with T4 ligase treatment, respectively. Lanes 4 and 5 compare $Fe_2(HPTB)(OH)(NO_3)_4/H_2O_2$ linearized plasmid without and with T4 ligase treatment, respectively. Lanes 6 and 7 compare plasmids linearized by $Fe_2(HPTB)(OH)(NO_3)_4/(O_2+$ascorbate) without and with T4 ligase treatment, respectively. The 1 Kb ladder is in lane 8.
Figures 3A, 3B:
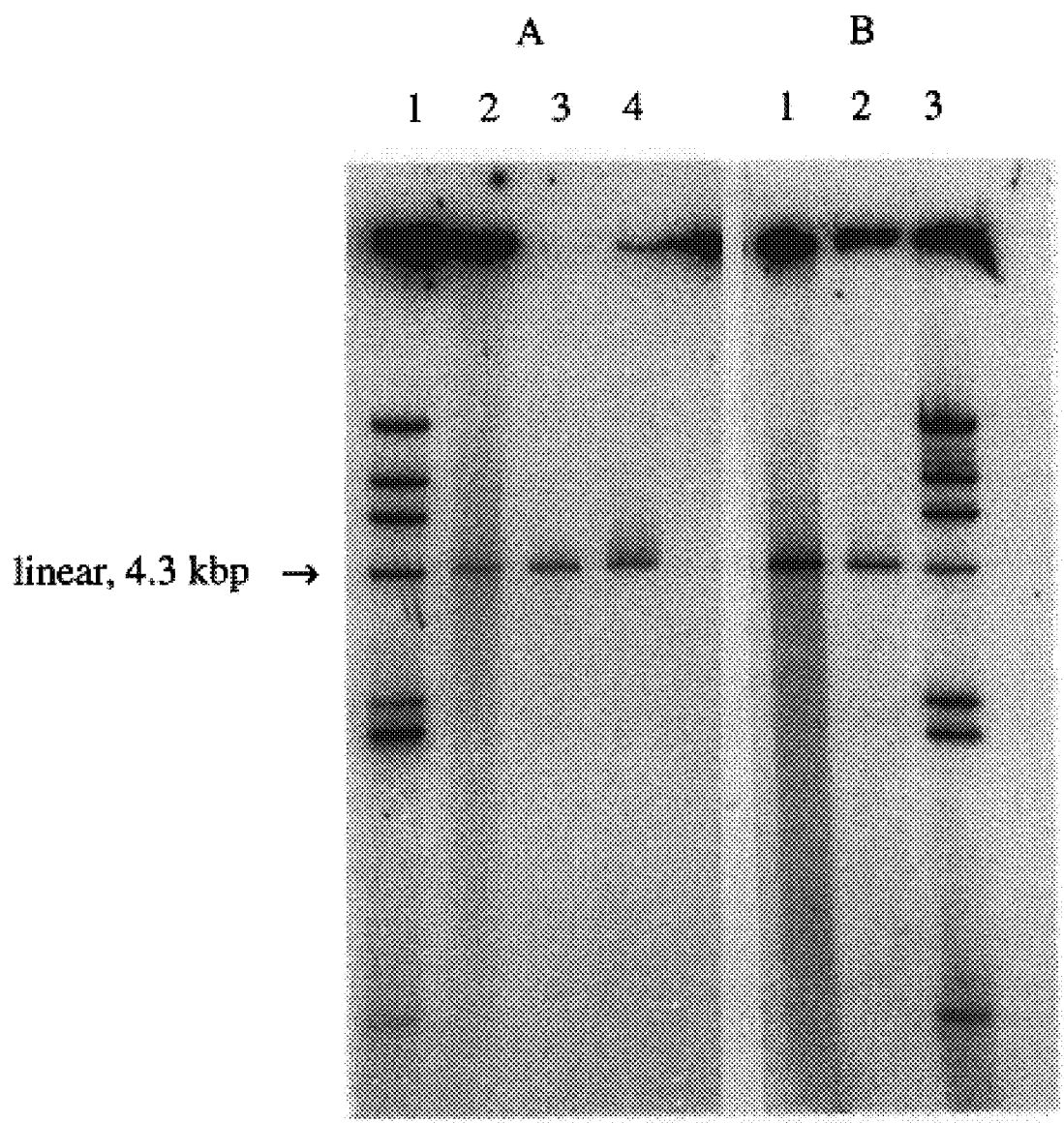
FIG. 3: End labelling experiments for linearized plasmid (50 ng/lane). On electrophoresis gel A are the 5'-end labelling results. Lane 1 is the Hind III $\lambda$ ladder. Lanes 2, 3 and 4 show the results of the 5'-end labelling experiments on pBR322 linearized by $Fe_2(HPTB)(OH)(NO_3)_4/H_2O_2$ (lane 2, densitometer area=1.45), Hind III (lane 3 densitometer area=1.31) or Pst I (lane 4 densitometer area=1.45). The 5'-end labels were incorporated by treatment with T4 polynucleotide kinase and [$\gamma$-$^{32}$P]dATP after dephosphorylation by alkaline phosphatase. Electrophoresis gel B shows the 3'-end labelling results using terminal deoxynucleotidyl transferase and [$\alpha$-$^{32}$P]ddCTP on $Fe_2(HPTB)(OH)(NO_3)_4/H_2O_2$ (lane 1, densitometer area=1.82) and Hind III (lane 2, densitometer area=1.78) linearized pBR322. The Hind III $\lambda$ ladder is in lane 3.

The present invention provides a method of cleaving nucleotide sequences using a new class of nucleotide cleaving agents. These cleaving agents typically cleave the nucleotide sequence at the sugar phosphate backbone, i.e., in a manner in which the nucleotide sequence is cut to leave a hydroxyl on one end and a phosphate on the other end. In this way, the resultant nucleotide sequence fragments are "intact" such that they can be religated or cloned. It is believed they operate using a nucleophilic displacement mechanism. Preferably, the nucleotide cleaving agents cleave the phosphate backbone yielding a 5' phosphate end and a 3' hydroxyl end.

Specifically, the present invention provides a method for cleaving a nucleotide sequence using a cationic metal complex having at least one, and typically one or two, polydentate ligand(s), with the nucleotide sequence. This may or may not occur in the presence of a dioxygen source. The cationic metal complex optionally may be capable of generating a nucleophilic peroxide in the presence of a dioxygen source.

The cationic metal complex can include any metal or metals of the Periodic Table of sufficient Lewis acidity to activate, e.g., bind, $H_2O_2$, although this does not mean that binding of $H_2O_2$ necessarily occurs in the method of the present invention. Preferably, the cationic metal complex is a dinuclear metal complex containing one or more metal centers of a divalent or trivalent metal ion. It is to be understood that any dinuclear complex of the present invention can include the same or two different metals. More preferably, the metal is a lanthanide series metal, or a metal from any of the following groups of the Periodic Table: Group IIIA, i.e., Group 13 (Al, Ga, In); Group IB, i.e., Group 11(Cu, Ag, Au); Group VB, i.e., Group 5 (V, Nb, Ta); Group VIIB, i.e., Group 7 (Mn, Tc, Re); Group VIIIB, i.e., Groups 8 (Fe, Ru, Os), 9 (Co, Rh, Ir), 10 (Ni, Pd, Pt). Of the Group IB, VB, VIIB, and VIIIB metals, the first row transition metals are preferred. Most preferably, the metal is a lanthanide series metal, a Group IIIA metal or a Group VIIIB metal. Of the Group IIIA metals, Ga is the most preferred, and of the Group VIIIB metals the iron triad is preferred, with Fe being more preferred, and Fe(III) being most preferred.

The cationic metal complex has at least one, and typically one or two, polydentate ligand(s), preferably a ligand having two tridentate chelating groups linked by a polyatomic chain. More preferably, this ligand contains chelating groups having aromatic rings, which enhance the hydrophobicity and specificity of the metal complex. The polydentate ligand can be represented by the formula $(R^1)(R^2)N-R^3-N(R^4)(R^5)$ (Formula I) wherein $R^3$ represents the polyatomic chain, i.e., linking group. $R^3$ is preferably a substituted or unsubstituted aliphatic or aromatic group having at least a 3-carbon chain, and typically a 3–5-carbon chain, capable of linking the two tridentate chelating groups. That is, although the linking group can have more than 3 carbons in the overall structure, the two tridentate chelating groups are directly linked preferably through a chain of no less than three carbon atoms and no more than five carbon atoms. In this way, thermodynamic and steric factors favor the chelation of two metal centers by the ligand. In this context, the aliphatic or aromatic group can be substituted with any substituent that does not adversely affect the function of the metal complex. Examples of such groups include —OH, —SH, alkyl groups (preferably $(C_{1-5})$alkyl groups), and the like. Such groups can also be capable of bonding to one or more of the metal centers, thereby enhancing the stability of the metal complex. Examples of suitable $R^3$ groups include —CH$_2$—CH(OH)—CH$_2$—, —CH$_2$CH$_2$—CH(OH)—CH$_2$CH$_2$—, —CH$_2$—CH(OH)—CH$_2$CH$_2$—, and —CH$_2$—C$_6$H$_3$(OH)—CH$_2$— (in which the aromatic ring is substituted by the —CH$_2$— groups in the 2 and 6 positions and the —OH group is at the 1 position). More preferably, $R^3$ is a substituted or unsubstituted $(C_{3-5})$alkylene group. Of the $(C_{3-5})$alkylene groups, —CH$_2$—CH(OH)—CH$_2$—, —CH$_2$CH$_2$—CH(OH)—CH$_2$CH$_2$—, and —CH$_2$—CH(OH)—CH$_2$CH$_2$— are preferred. Most preferably, $R_3$ is —CH$_2$—CH(OH)—CH$_2$—.

In Formula I, each of $R^1$, $R^2$, $R^4$, and $R^5$ may be the same or different and are Lewis basic groups, i.e., groups capable of coordinating to the metal of choice. Preferably, each of these groups contains one or more aromatic rings. Examples of such groups include a substituted or unsubstituted 2-benzimidazolylmethyl, substituted or unsubstituted 2-(2-benzimidazolyl)ethyl, substituted or unsubstituted 2-pyridylmethyl, substituted or unsubstituted 2-(2-pyridyl)ethyl, substituted or unsubstituted 2-imidazolylmethyl, and substituted or unsubstituted 2-(2-imidazolyl)ethyl. As used in this context, these groups can be substituted with any substituents that do not adversely affect the function of the metal complex. Specific examples of such groups include halides, alkyl groups (preferably $(C_{1-5})$alkyl groups), amino groups, carboxy groups, and the like. It is to be understood, however, that the substituent can actually enhance the function of the metal complex. For example, the substituent can be used to attach a nucleotide sequence recognition element that enhances the specificity of the metal complex for a specific sequence.

The metal complex can also include other ligands to form a stable complex. These ligands do not adversely affect the function of the metal complex, although they may enhance the function of the metal complex. Any ligand can be used that is easily displaceable by peroxide. Examples of suitable such ligands include hydroxide, nitrate, sulfate, perchlorate, carboxylate, and the like. Preferably, these ligands are hydroxide and nitrate ligands.

Specifically preferred complexes for use in the method of the present invention include the dinuclear complexes $Fe_2(HPTB)(OH)(NO_3)_4$, $Fe_2(HPTP)(OH)(NO_3)_4$, and $[Fe_2(HPTP)(OBz)](BPh_4)_2$. Although the cationic metal complexes used in the method of the present invention are typically prepared, isolated, and then combined with the nucleotide sequence of interest, it is believed that the metal complex could also be made in situ, at least to a limited extent, by combining the appropriate ligand with a source of the metal ion of choice.

The cationic metal complex described herein can operate in concert with a dioxygen source, i.e., a source of $O_2$, to effect cleavage of nucleotide sequences. For certain embodiments, as with $Fe_2(HPTB)(OH)(NO_3)_4$, $Fe_2(HPTP)(OH)(NO_3)_4$, and $[Fe_2(HPTP)(OBz)](BPh_4)_2$, the method occurs in the presence of a dioxygen source, which is preferably a peroxide, e.g., $H_2O_2$, or a reductant in combination with $O_2$. For other embodiments, this may or may not be required. The reductant is one that is capable of reducing the metal center of the metal complex, is a mild reducing agent, and is at least partially soluble in water. As used in this context, a "mild" reducing agent is one that is suitable for use in biological samples. Examples of such reductants include ascorbate, thiols, e.g., DTT, and 2-mercaptoethanol. For complexes in which the metal center is Fe(III), the reductant is preferably ascorbate or DTT.

The cationic metal complex described herein can be a nucleophilic peroxide-generating cationic metal complex, i.e., a cationic metal complex that is capable of generating a nucleophilic peroxide in the presence of a dioxygen source, although this is not a necessary requirement of the methods of the present invention. That is, the metal complex may be, although is not required, sufficiently reactive with $O_2$ and a reductant as described above, or $H_2O_2$ such that a nucleophilic peroxide is formed. As used herein, a "nucleophilic" peroxide is one with sufficient electron density to attack the phosphorus center in DNA. This reactivity can be determined in a variety of ways. The simplest way is to react a model nucleotide, such as a phosphate diester, e.g., bis(p-nitrophenyl) phosphate, with the metal complex and $H_2O_2$ in water. The formation of hydrolysis products is evidence that a nucleophilic peroxide is formed during the reaction. For example, the appearance of p-nitrophenolate anion conveniently monitored by a UV-vis spectrophotometer at 390 nm would indicate that the P—OR bond is cleaved. A more direct means of determining if a nucleophilic peroxide is formed results from labelling studies. For example, the incorporation of $^{18}O$ into the phosphate product when $^{18}O_2$ or $H_2^{18}O_2$ is used as the dioxygen source in the cleavage system would show that the dioxygen moiety attacks the P center in cleaving the P—OR bond.

The process of cleaving a nucleotide sequence is preferably carried out in water at a pH, temperature, with a concentration of reagents, and for a time effective to cleave the nucleotide sequence in its phosphate backbone. Typically, the conditions are chosen such that the cleavage occurs within less than about three hours, preferably, within less than about one hour, and more preferably instantaneously, i.e., within a few minutes. If radical scavengers are added to the reaction mixture, such as DMSO, formate, thiourea, mannitol, or glycerol, the reaction can be carried out longer without significantly degrading the nucleotide sequence being cleaved.

Organic solvents can be used in low concentrations, i.e., a sufficient amount to bring the metal complex into solution, but not so much as to denature the nucleotide sequence. The temperature at which the cleavage is carried out is preferably within a range of about −10° C. to about 100° C., more preferably about 0–40° C., and most preferably about 20–37° C. The pH at which the cleavage is carried out is preferably within a range of about 5.5–9.0, and more preferably at about a pH of about 8. The reaction can be conveniently carried out in the atmosphere.

Typically, for a 0.2 microgram sample of DNA, the amount of cationic metal complex is preferably about 0.5–50 micromoles, more preferably about 0.5–10 micromoles, and most preferably about 5–10 micromoles. The molar ratio of reductant to cationic metal complex is preferably about 1–1000:1, more preferably about 1–100:1, and most preferably about 100:1. With too much reductant or cationic complex, degradation of the nucleotide sequence to be cleaved can occur.

Although the complexes of the present invention can be used to cleave any type of nucleotide sequence, whether double- or single-stranded, they advantageously cleave double-stranded supercoiled DNA into fragments that can be religated. Certain preferred embodiments of the metal complexes used in the method of the present invention cause site-specific cleavage of double-stranded supercoiled DNA. As used herein, "supercoiled" DNA refers to twisted, covalent, closed circular DNA molecules. For example, $[Fe_2(HPTB)(OH)(NO_3)_2](NO_3)_2$ and $H_2O_2$ specifically cleaves the plasmid pBR322 between base pairs 3485 and 3489. Although the inventors do not wish to be held to any particular theory, it is believed that this is the result of a size and shape relationship of the cleaving agent with the DNA topology.

If desired, the site specificity of the metal complex cleaving agents of the present invention can be altered by tethering. That is, they can be tethered to molecules, i.e., herein referred to as "recognition elements," that recognize specific nucleotide sequences. Suitable recognition elements include nucleotide sequences, antibiotics, and proteins. Examples of such recognition elements and tethering methods are well known to those of skill in the art. Some of these are disclosed in Dervan et al., U.S. Pat. No. 4,795,700, which is incorporated herein by reference.

The point of tethering occurs at the polydentate ligand. Within this ligand the point of tethering can occur at one of the tridentate chelating groups or at the polyatomic chain. In one particular embodiment, if double-stranded DNA is to be cleaved at a particular site, the recognition element is a nucleotide sequence that is complementary to a portion of one of the nucleotide strands. In this way, a triple helix is formed at the area of attachment of the recognition elements.

Thus, the metal complexes of the present invention can be used for cleavage of DNA or RNA, preferably sequence-specific, i.e., site-specific cleavage, to prepare smaller nucleotide fragments for cloning, sequencing, and other molecular biology applications. Additionally, they can be used as diagnostic tools for detecting the presence of certain DNA or RNA viruses, such as hepatitis virus or measles virus, in biological fluids or tissue samples. They can also be used to detect the presence of specific genes, e.g., oncogenes and other genes associated with specific genetic abnormalities, in biological fluid or tissue samples. When a metal complex of the present invention is used as a diagnostic tool, the DNA or RNA can be first extracted using conventional techniques. The metal complex having a specific recognition element is then combined with the polynucleotides under conditions that allow hybridization of the recognition element to the target sequence if present. The hybridized product is then detected using appropriate means known to those of skill in the art. Not only can the metal complexes of the present invention be used as diagnostic tools, but they can be used as therapeutic tools. That is, they can be used to destroy target molecules, e.g., viruses and oncogenes. For example, the metal complexes can be designed to target and cleave messenger RNA sequences that encode proteins linked to cancer or other diseases.

EXPERIMENTAL EXAMPLES

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

Materials: Chemicals used in this study were obtained from the following sources: from Aldrich Chemical Co., ascorbate, DTT, ferric nitrate, MMPP (magnesium monoperoxyphthalate), mannitol, oxone (potassium peroxymonosulfate) and thiourea; from Sigma (St. Louis, Mo.), chloramphenicol, tetracycline, 1,2-diaminobenzene, 2-hydroxy-1,3-diaminopropcine tetraacetic acid, Tris•HCl, and SDS-lauryl sulfate; from EM Science (Gibbstown, N.J.), ethanol, glycerol, methanol, NaOH, and acetone; from Fisher Scientific, acrylamide, agarose, ascorbate, cesium chloride, DMSO (dimethylsulfoxide), EtdBr, N,N,N',N'-tetramethylethylenediamine and urea; from Mallinckrodt (Paris, Ky.), potassium acetate; and from J. T. Baker (Phillipsburg, N.J.), sodium acetate. Restriction enzymes Ava I, Hind III, Pst I and Sal I, BSA, T4 DNA ligase, terminal deoxynucleotidyl transferase and topoisomerase I were purchased from the Promega Corporation (Madison, Wis.). Sequenase was purchased from United States Biochemical Company (Cleveland, Ohio), T4 polynucleotide kinase from New England Biolabs (Beverly, Mass.), and bacterial alkaline phosphatase and the 1 Kb ladder from Gibco BRL (Gaithersburg, Md.). Isotopically labelled nucleotides [α-$^{32}$P]dCTP, [α-$^{32}$P]ddCTP, [γ-$^{32}$P]dATP, adenosine 5'-[α-[$^{35}$S]thio]triphosphate and adenosine 5-[γ-[$^{35}$S]thio] triphosphate were purchased from Amersham (Arlington Heights, Ill.).

Ligand Synthesis: HPTB was synthesized as follows: 1,2-Diaminobenzene (10.55 grams, 97.0 mmol) was ground into a fine powder and intimately mixed with 2-hydroxy-1, 3-diaminopropane-tetraacetic acid (5.0 grams, 16.0 mmol $(HOOCCH_2)_2N—CH_2CH(OH)CH_2—N(CH_2COOH)_2)$). The mixture was heated at 170–180° C. for 1 hour, until effervescence had stopped. After cooling, the resulting red glass was taken up in dilute (≠4M) HCl (≠150 ml or until dissolved), and a grayish blue precipitate was slowly formed. After the solution was filtered and this precipitate was washed with acetone several times, the precipitate was then dissolved in water and charcoal was added to approximately 5% and the mixture refluxed 5–10 minutes. The solution was filtered to remove the charcoal, while hot. The solution was neutralized with dilute ammonia. The off-white precipitate was collected and recrystallized from acetone when necessary, and vacuum dried.

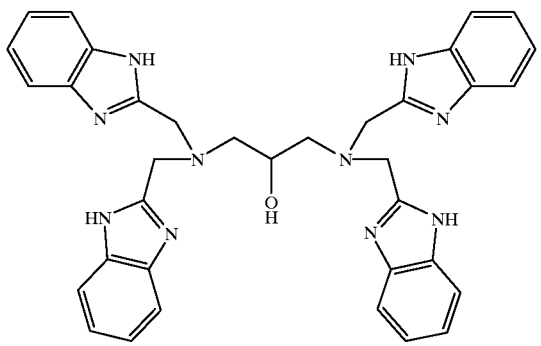

The tetrakis(2-pyridylmethyl) analogue of the HPTB ligand, i.e., HPTP or N,N,N',N'-tetrakis(2-pyridylmethyl)-2-hydroxy-1,3-diaminopropane (the benzimidazoles are changed to pyridines), was prepared in the following manner: a 14.7% aqueous solution of bis(2-pyridylmethyl)amine (3.06 g, 15.4 mmol) was adjusted to about pH 8 by adding 6 N HCl. The solution was maintained at about 70–75 °C. and pH 8 while 0.71 g (7.7 mmol) epichlorohydrin was added slowly to the solution. After 4 h, the solution was then cooled to about 0° C., and 70% HClO$_4$ was added to the solution until no more yellow precipitate formed. After filtration, the yellow precipitate was washed with cold MeOH and dried in vacuo. $^1$H NMR and mass spectrometry indicated that the yellow solid was HPTP•4HClO$_4$ (3.51 g; yield, 53.4%). $^1$H NMR (D$_2$O), δ (ppm): 2.7 (m, 4H), 4.3 (m, 9H), 7.9 (m, 8H), 8.5 (t, 4H), 8.7 (d, 4H).

HPTP was prepared as described by Dong et al., *J. Amer. Chem. Soc.*, 115, 1851–1859 (1993), specifically by the reaction of epichlorohydrin with bis(2-pyridylmethyl)amine. A 14.7% aqueous solution of bis(2-pyridylmethyl)amine (3.06 g, 15.0 mmol) was adjusted to about pH 8 by adding 6N HCl. The solution was maintained at about 70–75° C. and pH 8 while 0.71 g (8.0 mmol) epichlorohydrin was added slowly to the solution. After 4 h, the solution was then cooled to about 0° C., and 70% HclO$_4$ was added to the solution until no more yellow precipitate formed. After filtration, the yellow precipitate washed with cold MeOH and dried in vacuo.

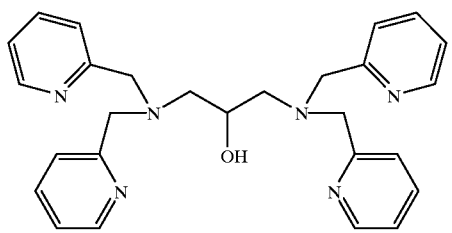

Iron Complex Synthesis: The complex [Fe$_2$(HPTB)(OH)(NO$_3$)$_2$](NO$_3$)$_2$, which interacts with H$_2$O$_2$ to form a 1:1 adduct, was synthesized according to the procedure of Brennan et al., *Inorg. Chem.*, 30, 1937–1943 (1991), which is incorporated herein by reference. HPTB (0.2 mmol) was dissolved in 20 ml ethanol, and 0.4 mmol Fe(NO$_3$)$_3$•9H$_2$O was added. Upon standing the dark orange solution yielded dark orange needles and platelike crystals. The crystals were washed with EtOH and vacuum dried to powder form. This cationic complex can be represented as follows, wherein HPTB is the chelating ligand:

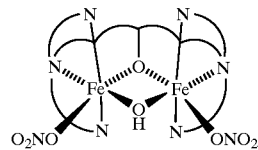

The corresponding diferric species, Fe$_2$(HPTP)(OH)(NO$_3$)$_4$, which forms a spectroscopically similar species when H$_2$O$_2$ is added, was prepared analogously to the HPTB complex described above.

Fe$_2$(HPTB)(OH)(NO$_3$)$_4$ was prepared by dissolving HPTB (0.15 g, 0.2 mmol) in 20 ml EtOH and then adding Fe(NO$_3$)$_3$•9H$_2$O (0.20 g, 0.4 mmol). Upon standing, the dark orange solution yielded dark orange needles and platelike crystals.

Fe$_2$(HPTP)(OMe)(NO$_3$)$_2$(ClO$_4$)$_2$ was synthesized by addition of a solution of Fe(NO$_3$)$_3$•9H$_2$O (0.066 g, 0.16 mmol) in 10 ml MeOH to a solution of HPTP•4HClO$_4$ (0.05 g, 0.06 mmol) and Et$_3$N (0.04 ml, 0.29 mmol) in 10 ml of MeOH. Greenish-yellow platelike crystals were collected after leaving 40 h in vacuum desiccator.

The diferric species Fe$_2$(HPTP)(OBz)(BPh$_4$)$_2$ was prepared as described by Dong et al., *J. Amer. Chem. Soc.*, 115, 1851–1859(1993), which is incorporated herein by reference. Specifically, it was prepared under argon by dissolving HPTP•4HClO$_4$ (0.214 g, 0.25 mmol), HOBz (benzoic acid, 0.0305 g, 0.25 mmol), and Et$_3$N (0.139 g, 1.37 mmol) in 10 ml of methanol and transferring the solution anaerobically to solid Fe(BF$_4$)$_2$•6H$_2$O (0.169 g, 0.50 mmol). The addition of a degassed methanol solution of NaBPh$_4$ (0.171 g, 0.50 mmol, 10 ml) yielded a yellow precipitate which was filtered off, dried in vacuo, and recrystallized from acetonitrile and diethyl ether.

DNA Isolation: Plasmid pBR322 was purchased from Pharmacia (Piscataway, N.J.) and transformed into *E. coli* strains JM109 and HB101 obtained from the American Type Culture Collection (also available from the Genetic Stock Culture Collection). This was done using CaCl$_2$ according to the procedure of Hanahan, *DNA Cloning: A Practical Approach*, 1, 109–136 (1985), which is incorporated herein by reference. JM109 or HB101 cells were grown in 20 ml Luria-Bertani (LB) media to an optical density of 0.13–0.15. The cells were spun 5 minutes at 5,000×g at 4° C. The media was decanted and the cells resuspended in 10 ml of 10 mM Mops, pH=7.0 and 10 mM rubidium chloride. The cells were pelleted as described above. The supernatant was decanted and the cells resuspended in 10 ml of 10 mM Mops, pH=6.5, 50 mM CaCl$_2$, and 10 mM rubidium chloride. The cells were placed on ice for 30 minutes. The cells were then pelleted as described above, the supernatant decanted and the pellet resuspended in 1.0 ml of 10 mM Mops, pH=6.5, 50 mM CaCl$_2$ and 10 mM rubidium chloride. These competent cells (200 μl) were added to an Eppendorf tube and 3 μl DMSO was added by pipet. The tube was placed on ice. DNA (10–20 μl, 0.15–0.20 μg DNA) was added and the tube left on ice for 30 minutes. The cells were then heated at exactly 42° C. for 1–2 minutes and 1.0 ml LB media was added. The cells were shaken gently at 37° C. for 60 minutes. These transformed cells (200 μl) were plated on LB agar plates containing tetracycline.

The cells were grown in Luria-Bertani broth containing tetracycline, 15 μg/ml prepared by a 12.5 mg/ml stock of tetracycline hydrochloride in ethanol/water (50% v/v), filter sterilized and stored at −20° C. They were then amplified with 2.5 ml chloramphenicol per 500 ml culture (34 mg/ml ethanol, filter sterilized) after the optical density at 600 nm reached 0.4. The cells were then shaken at 37° C. for an additional 12–16 hours. The plasmid was purified according to a modified procedure of Birnboim et al., *Nucl. Acids. Res.*, 7, 1513–1523 (1979), which is incorporated herein by reference. The cells were spun at 5,000×g for 5 minutes to pellet, and then resuspended into two centrifuge bottles, with 20 ml 50 mM glucose, 25 mM Tris•HCl pH=8.0, 10 mM EDTA each. Freshly prepared 0.2 M NaOH and 1% SDS solution (40 ml) was added and the tubes were mixed gently by inversion and iced for 30 minutes. Ice cold 5 M potassium acetate (30 ml, pH=4.8) was added and the solution mixed by inversion and kept on ice for 30 minutes. The cell debris was pelleted at 8,000 rpm, 4° C. for 25 minutes. The resulting supernatant, which contained the DNA, was filtered through four layers of cheese cloth and the supernatant poured into new centrifuge tubes. Isopropanol (70 ml) was added and the tubes placed in the −20° C. freezer for 2–3 hours. The solution was then spun at 8,000 rpm for 25 minutes. The DNA pellet was washed with 70% ethanol and then dried. The pellet was dissolved in 8.0 ml of TE buffer (10 mM Tris, pH=8.0 and 1 mM EDTA). The DNA was purified in a CsCl gradient, by the addition of 1 gram of solid cesium chloride per 1 ml DNA solution. Ethidium bromide (EtdBr, 0.8 ml of a solution of 10 mg/ml in $H_2O$) was added for every 10 ml DNA solution. The solution was transferred to a sealable centrifuge tube, which was filled with paraffin oil and sealed. The tubes were spun at 50,000 rpm for 36 hours at 20° C. The plasmid band was removed and the EtdBr removed with $H_2O$ saturated isobutanol. The EtdBr-free aqueous solution was dialyzed against several changes of TE buffer. The purity and quantity of DNA were determined by measuring the $A_{260}/A_{280}$ ratio, using a Hoefer fluorometer, which has been standardized, and gel electrophoresis.

Example 1

Linearization of pBR322 with $Fe_2(HPTB)(OH)(NO_3)_4$, and Related Complexes

The cleavage of pBR322 by $Fe_2(HPTB)(OH)(NO_3)_4/H_2O_2$ was accomplished by mixing (in order) 1 μl (0.15 mg/ml) pBR322, 1 μl Tris•HCl (0.1 M, pH=8.0) buffer, 1 μl (0.1 mM) $Fe_2(HPTB)(OH)(NO_3)_4$, 6 μl $H_2O$ and 1 μl 9.0 mM $H_2O_2$ in a room temperature, instantaneous reaction. The cleaved DNA products were subjected to electrophoresis on a 1% agarose gel in TAE (40 mM Tris-acetate, 1 mM EDTA) at 70 volts for 5 hours and stained with 0.5 μg/ml EtdBr solution.

The amount of DNA was quantitated by photographing the fluorescence under UV light and analyzing the band intensities using a Pharmacia densitometer. The linearized pBR322 was recovered from the agarose gel by electroelution of the excised gel fragment using an elutrap in TAE buffer for 3 hours at 150 volts, followed by phenol:chloroform extraction and precipitation with 1/10 volume 3.0 M NaOAc and 2 volumes of ethanol as discussed in Maniatis et al. in *Molecular Cloning, A Laboratory Manual* (Cold Spring Harbor Laboratory, Cold Spring Harbor, N.Y.) at pp. 149–172 (1982), which is incorporated herein by reference. The tubes were left overnight at −20° C. and spun at 12,000×g for 25 minutes. The supernatant was decanted off and the resulting pellet, which is the DNA, was gently washed with 70% ethanol, respun at 12,000×g in a batch top microfuge for 10 minutes and the ethanol decanted off. The pellet was dried in a speed vacuum and resuspended in 50 μl TE (10 mM Tris, 1 mM EDTA, pH=8.0) and the concentration determined as described above.

Control experiments with $Fe(EDTA)/H_2O_2$ were performed under conditions identical to those of $Fe_2(HPTB)(OH)(NO_3)_4$. When present, HO• scavengers such as DMSO, formate, thiourea, mannitol or glycerol were introduced to afford a final concentration of 0.4 M prior to $H_2O_2$ addition. In other experiments, $H_2O_2$ was replaced by oxygen transfer agents, oxone or MMPP, or the reductants ascorbate or DTT. All reactions were carried out in the atmosphere. These experiments suggested that the hydroxyl radical HO• was not involved in the DNA cleavage.

The possibility of oxidative base loss, i.e., H-abstraction from ribose, resulting in release of DNA base was tested by the adding 0.1 M piperidine to the pBR322 cleavage reaction solutions and heating 10 minutes at 65° C. prior to gel electrophoresis. The addition of base (piperidine) caused strand scission of the oxidized ribose moiety as depicted by the appearance of numerous small pBR322 fragments. This showed that there were base-sensitive lesions, i.e., sites susceptible to oxidation.

Analysis for malondialdehyde-like products was performed by the addition of 0.6% 2-thiobarbituric acid, heating the sample in boiling $H_2O$ for 20 minutes and analyzing the sample spectrophotometrically at 532 nm according to the procedure of Waravdeker et al., *J. Biol. Chem.* 234, 1945–1951 (1959), which is incorporated herein by reference. No malondialdehyde adducts resulting from sugar oxidation, i.e., oxidative cleavage of DNA, were observed.

Table 1 lists the amounts of supercoiled, nicked and linear pBR322 obtained in each experiment as quantitated by densitometry upon the addition of various concentrations of $Fe_2(HPTB)(OH)(NO_3)_4$ and $H_2O_2$ in a 1:100 ratio to supercoiled pBR322 (0.015 mg/ml). The addition of 10 μM $Fe_2(HPTB)(OH)(NO_3)_4$ afforded the maximum amount of linearized plasmid (31% yield), without significant further degradation of the DNA (as indicated by a lack of smearing on the gel). Similar results were obtained (34% yield) at 10 μM $Fe_2(HPTB)(OH)(NO_3)_4$ when $H_2O_2$ was replaced by $O_2$ and 10.0 mM reductant (ascorbate or DTT).

TABLE 1

Cleavage of pBR322 with $Fe_2(HPTB)(OH)(NO_3)_4$

| [$Fe_2(HPTB)(OH)(NO_3)_4$]* | % Supercoiled | % Nicked | % Linear |
|---|---|---|---|
| 0.0 μM | 91 | 9 | 0 |
| 0.5 μM | 89 | 11 | 0 |
| 1.0 μM | 69 | 31 | 0 |
| 5.0 μM | 21 | 61 | 18 |
| 10.0 μM | 0 | 69 | 31 |
| 50.0 μM** | 0 | 33 | 35 |

*The [$Fe_2(HPTB)(OH)(NO_3)_4$] was varied while the ratio between the [$Fe_2(HPTB)(OH)(NO_3)_4$] and [$H_2O_2$] remained at 1:100.
**At ≧50.0 μM $Fe_2(HPTB)(OH)(NO_3)_4$, linearized plasmid is cut further (a smear on the gel).

For comparison, the addition of 1.0 mM FE(EDTA) (100-fold higher concentration) and 9.0 mM $H_2O_2$ was required to afford 93% nicked plasmid and 7% linearized plasmid. The Fe(EDTA)-catalyzed cleavage reactions were almost completely inhibited by the presence of HO• scavengers (0.4 M DMSO, formate or glycerol). In contrast, the presence of DMSO, thiourea, mannitol, formate or glycerol did not affect the cleavage activity of $Fe_2(HPTB)(OH)(NO_3)_4$, suggesting that diffuse HO• was not involved in this reaction.

Parallels to Fe-bleomycin-mediated cleavage, as discussed by Rabow et al., *J. Am. Chem. Soc.,* 112, 3196–3203 (1990); Rabow et al., *J. Am. Chem. Soc.,* 112, 3203–3208 (1990); Sugiyama et al., *J. Am. Chem. Soc.,* 107, 4104–4105 (1985); and Sugiyama et al., *Biochemistry,* 27, 58–67 (1988), were also explored. Treatment of the linearized plasmid with piperidine resulted in further strand scission, indicating the presence of base-sensitive lesions, but we could not detect the formation of malondialdehyde-like products with 2-thiobarbituric acid according to the procedure used by Sausville et al., *Biochemistry,* 17, 2746–2754 (1978). In contrast, a previously reported experiment of the cleavage of calf thymus DNA with $H_2O_2$ and $Fe_2(HPTB)$ $(OH)(NO_3)_4$ for 1–2 days showed that the DNA was cleaved oxidatively as a result of the formation of pink colored malondialdehyde adducts of sugar oxidation products. Nishida et al., *Inorg. Chim. Acta,* 163, 9–10 (1989). There was no evidence of the cleavage of the DNA phosphate backbone. Furthermore, oxygen transfer agents oxone and MMPP were ineffective substitutes for $H_2O_2$ in the $Fe_2$ $(HPTB)(OH)(NO_3)_4$ cleavage reaction (FIG. 1). Taken together, our results suggest that the double stranded cleavage mediated by $Fe_2(HPTB)(OH)(NO_3)_4$ does not occur by an oxidative mechanism. The contrary Nishida et al. results are believed to be a result of possible contaminants, the fact that DNA is not stable when exposed to ambient conditions for 1–2 days, or other potential experimental errors.

The cleavage of pBR322 by $Fe_2(HPTP)(OMe)(NO_3)_2$ $(ClO_4)_2/H_2O_2$ was accomplished in a similar manner. Similar to Fe(EDTA), the HPTP complex did not cleave pBR322 in the presence of hydroxyl radical scavengers like DMSO.

Example 2

Labelling of $Fe_2(HPTB)(OH)(NO_3)_4/H_2O_2$ linearized pBR322

The linearized plasmid derived from treatment with $Fe_2$ $(HPTB)(OH)(NO_3)_4$ was labelled at the 5'-end with T4 polynucleotide kinase and $\gamma$-$^{32}$P-labelled dATP following dephosphorylation by bacterial alkaline phosphatase (GIBCO BRL protocols). The dephosphorylation reaction was initiated by the addition of 150 units bacterial alkaline phosphatase to a solution containing 50 mM Tris•HCl (pH=8.0), 1 mM $ZnCl_2$, and the DNA. The reaction proceeded at 37° C. for 60 minutes. The reaction was quenched by adding 0.1% SDS and 100 $\mu$g/ml proteinase K and heating at 37° C. for 30 minutes. The solution was extracted with phenol/chloroform twice and once with chloroform to remove the bacterial alkaline phosphatase. The aqueous DNA layer was then precipitated with 0.1 volume sodium acetate (3.0 M) and 2.5 volumes ethanol. The tube was left at −20° C. overnight and DNA pelleted by centrifugation described earlier. The 5'-end was then labelled by addition of 20 units of T4 polynucleotide kinase to 10 mM DTT, 0.3 $\mu$M ATP, 50 mM Tris•HCl (pH=7.6), 10 mM $MgCl_2$, 50 pmol [$\gamma$-$^{32}$P] dATP and dephosphorylated DNA. The reaction was incubated at 37° C. for 30 minutes. It was terminated by addition of 1 $\mu$l of 0.5 M EDTA and precipitated as above with 0.5 volume of M ammonium acetate (7.5 M) and 2.5 volumes of ethanol.

3'-End labelling of the linearized plasmid was effected using terminal deoxynucleotidyl transferase and $\alpha$-labelled dCTP or ddCTP according to the procedure of Ausubel et al., *Current Protocols in Molecular Biology,* Greene Publishing Associates and Wiley Interscience, NY, pp. 3.4.1–3.4.9 (1987), which is incorporated herein by reference. Briefly, this involved the addition of 8 mM $MgCl_2$, 0.33 mM $ZnSO_4$, 60 $\mu$Ci[$\alpha$-$^{32}$P]dCTP or ddCTP, 100 mM potassium cacodylate (pH=7.2), 2 mM $CoCl_2$, 0.2 mM DTT, and DNA to 15 units terminal deoxynucleotidyl transferase and incubating 37° C. for 60 minutes. The reaction was stopped by addition of 1 $\mu$l of 0.5 M EDTA and a double 7.5 M ammonium acetate/ethanol precipitation, as described above.

For comparison, Hind III linearized pBR322 was subjected to analogous labelling protocols.

Example 3

This example shows how to tether a metal complex to a sequence specific recognition element, such as an oligonucleotide. The dinucleating ligand, such as HPTB or HPTP, can be attached to the nucleotide sequence at various positions. One such example is as follows:

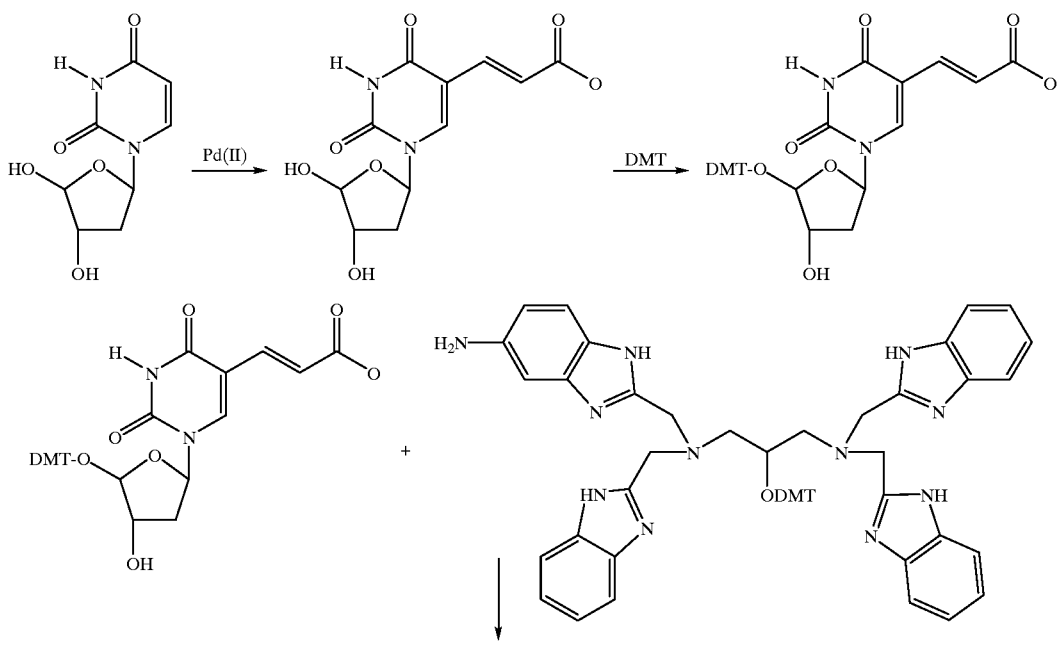

-continued

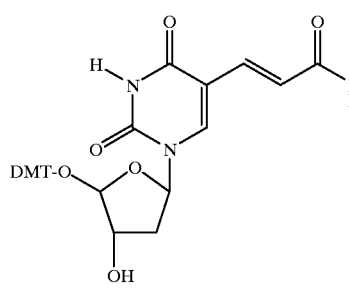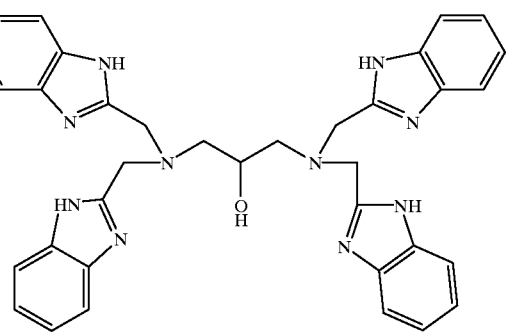

The first step in this process utilizes palladium (II) coupling chemistry and methyl acrylate in order to introduce alkyl side chains at carbon five of uridine, deoxyuridine, cytosine or deoxycytosine via the carbon five mercury or halogen derivatives, according to the method described in Langer et al., Proc. Nat. Acad. Sci., 78(11), 6633–6637 (1981), which is incorporated herein by reference. This nucleoside is then hydrogenated to selectively reduce the exocyclic double bond. The 5'-hydroxyl group of this nucleoside is protected with dimethoxytrityl chloride (DMT), according to the method described in H. G. Khorana, Science, 203, 614–625 (1970), which is incorporated herein by reference. The nucleoside can then be combined with modified HPTB.

The modified HPTB ligand is synthesized using the procedure outlined above but with 1 equivalent of 1,2-diamino-4-nitrobenzene and 3 equivalents diaminobenzene in place of the 4 equivalents of diaminobenzene. The hydroxyl group of this product is then protected with DMT. The nitro group of the resulting ligand is reduced to $NH_2$ using a Raney nickel reaction, as described in J. S. Prizey, Synthetic Reagents, 2, 175–311 (1974), Halsted Press, NY, which is incorporated herein by reference. The modified nucleoside is combined with this modified HPTB ligand to produce a 5'-DMT-T*-HPTB ligand, as shown above.

The DNA oligonucleotide is synthesized as follows. A 19-mer nucleotide-HPTB containing the 5'-DMT-T*-HPTB ligand is produced by the manual solid phase phosphoramidite method using published procedures, beginning with the 5'-DMT-T*-HPTB bound to a silica support (Matteucci et al., J. Am. Chem. Soc., 103, 3185–3191 (1981)) and Beaucage et al., Tetrahedron Lett., 22, 1859–1862 (1981)). The 5'-DMT-T*-HPTB is coupled by the tenth addition cycle as follows: 80 mg (79 μmol of nucleoside) dissolved in $CHCl_3$ (100 μl) and diisopropyl ethylamine (100 μl) and reacted with chloro-N,N-dimethylaminomethoxyphosphine (20 μl, 160 μmol) under Argon for 4 hours. The mixture is dissolved in EtOAc (1 ml) rinsed with saturated aqueous NaCl (1 ml), dried with $Na_2SO_4$ and concentrated. The resulting form is stored under vacuum (0.2 Torr) for 24 hours, then activated with 0.5 M tetrazole in $CH_3CN$ (0.6 ml) and coupled (15 minutes) to the protected, silica bound, 5-detritylated 10 mer CAGGCACCGT (SEQ ID NO:1). The subsequent DMT cleavage (5% dichloroacetic acid in toluene) monitored spectrophotometrically. Other oligonucleotide synthesis have been described elsewhere (Dorman et al., Tetrahedron, 40, 95–102 (1984); Adams et al., J. Am. Chem. Soc., 105, 661–663 (1983)).

The crude DNA-HPTB probe obtained is lyophilized and purified by electrophoresis (450 v, 22 hours) on a 2 mm thick 20% polyacrylamide gel (Maxam et al., Methods Enz. 65, 499–560 (1980)). The major UV-absorbing band is cut out and eluted with $H_2O$ at 60° C. for 24 hours, then eluted through Sephadex G10-120. The probe is then sequenced by Maxam-Gilbert chemical sequencing methods.

DNA cleavage experiments are carried out as described above. A few hundred base pair fragment containing the DNA probe recognition element will be $^{32}$P-end labelled and reacted with the DNA-HPTB probe, containing $Fe^{+3}$ and $H_2O_2$. The resulting fragments will be run on a polyacrylamide electrophoresis gel, to determine the specificity and ends produced.

Example 4

Hydrolytic Cleavage of DNA by $Ce_2HPTA$

We sought to ascertain the mechanism of cleavage of DNA by $Ce_2HPTA$ (HPTA=2-hydroxypropane-1,3-diamine tetraacetic acid) by examining the DNA cleavage products of suitably end-labeled restriction fragments using high resolution polyacrylamide gel electrophoresis. The nature of the ends formed from the cleavage by $Ce_2(HPTA)$ can be compared with those of the cleavage products from Maxam and Gilbert and DNase I reactions. The Maxam and Gilbert reactions produce 3'-phosphate end products and the DNase I reaction produces 3'-hydroxy end products, which can be visualized by using a 5'-end labeled DNA restriction fragment. With 3'-end labeled DNA restriction fragments, information about the 5'-ends of the DNA can be obtained. In this case both the Maxam and Gilbert and DNase I reactions give 5'-phosphate ends.

Figure 4A:
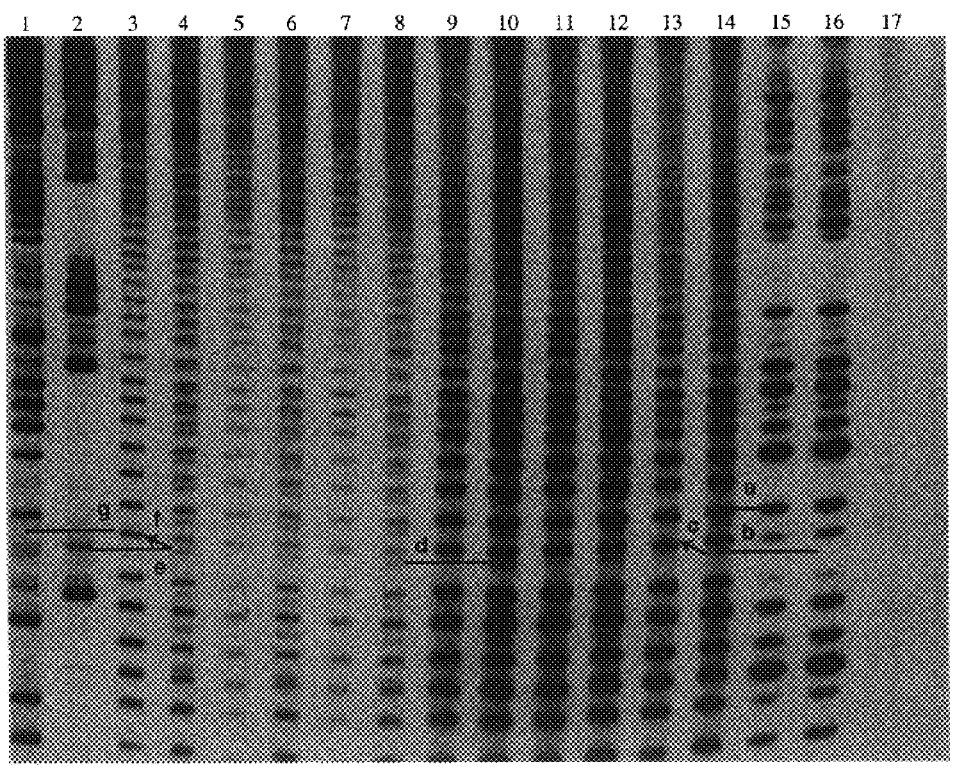
FIG. 4a: High resolution denaturing PAGE gel of cleavage products of a 5'-end-labelled 172 -bp restriction fragment by treatment with $Ce_2(HPTA)$ and La(III). Lane 1, C&T Maxam and Gilbert sequence; lane 2, G Maxam and Gilbert sequence; lanes 3, 5, & 7, La(III) cleaved DNA after treatment by T4 polynucleotide kinase; lanes 4, 6, & 8, La(III) cleaved DNA; lanes 9, 11, & 13, $Ce_2(HPTA)$-cleaved DNA after treatment by T4 polynucleotide kinase; lanes 10, 12, & 14, $Ce_2(HPTA)$ cleaved DNA; lane 15, DNA cleaved by DNase I; lane 16, DNA cleaved by DNase I; lane 17, control DNA. The line under a shows that the $Ce_2(HPTA)$ cleaved DNA comigrate with the DNase I generated cleavage products. The line under b shows the minority products of the $Ce_2(HPTA)$ reaction do not comigrate with the products of the DNase I reaction. The arrow under c indicates that the minority products of the $Ce_2(HPTA)$ reaction shift upon treatment with T4 polynucleotide kinase to the majority products which comigrate with the DNase I reaction products. The line under d shows that the minor products of the $Ce_2(HPTA)$ reaction comigrate with the minority products of the La(III) reaction. The line over e indicates that the minority product of the La(III) reaction comigrates with the products of the Maxam and Gilbert reactions. The arrow under f shows that the minority products of the La(II) reaction shift upon treatment with T4 polynucleotide kinase. The majority products of the La(III) reaction, as shown by line g, do not comigrate with the products of the Maxam and Gilbert reactions.

Cleavage reactions were carried out on a 5'-end labeled 172-bp DNA restriction fragment derived from the treatment of Litmus 29 plasmid DNA with Hind III and Pvu II. The major products of the $Ce_2(HPTA)$ reaction comigrate with the products of DNase I-catalyzed cleavage, indicating the presence of 3'-OH ends, as illustrated by line a of FIG. 4a. There is a minor population of cleavage products that comigrate with the Maxam and Gilbert reaction products, which possess a 3'-$OPO_3$ end (FIG. 4a, lines b and d). Treatment of the $Ce_2(HPTA)$-cleaved DNA with T4 polynucleotide kinase selectively dephosphorylates the 3'-end of the DNA and causes the 3'-$OPO_3$ bands to coalesce with the 3'-OH bands (FIG. 4a, arrow c). Only products with 3'-OH or 3'-$OPO_3$ ends are observed; no band appears that corresponds to a phosphoglycolate or other product that would indicate the participation of an oxidative reaction pathway.

Figure 4B:
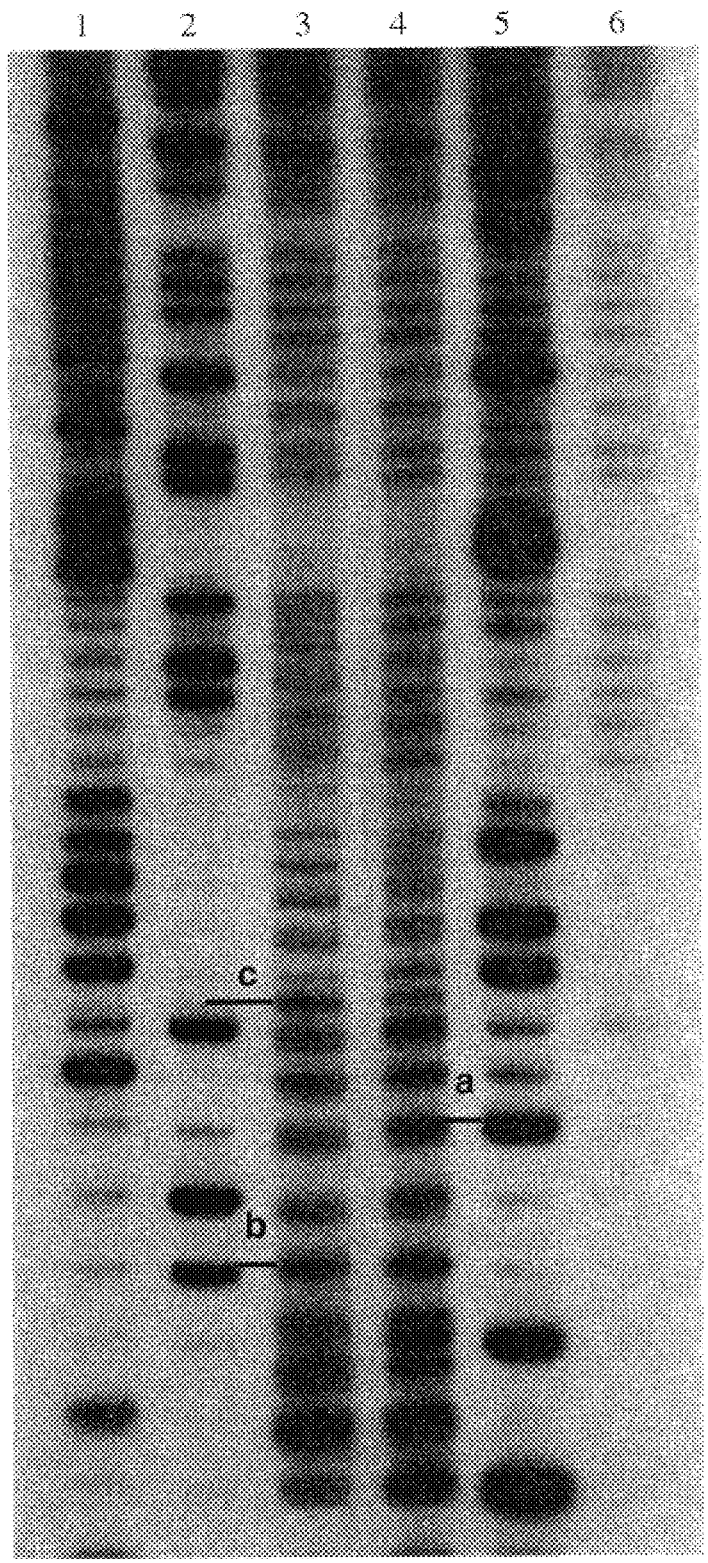
FIG. 4b: High resolution denaturing PAGE gel of cleavage products of a 3'-end-labelled 181-bp restriction fragment by treatment with $Ce_2(HPTA)$. Lane 1, C&T Maxam and Gilbert sequence; lane 2, G Maxam and Gilbert sequence; lane 3, $Ce_2(HPTA)$ cleaved DNA after treatment by T4 polynucleotide kinase; lane 4, $Ce_2(HPTA)$ cleaved DNA; lane 5, DNA cleaved by DNase I; lane 6, control DNA. The line under a shows that the $Ce_2(HPTA)$ cleaved DNA comigrates with the DNase I generated cleavage product. The line under b shows that the $Ce_2(HPTA)$ cleaved DNA also matches the products from the Maxam and Gilbert sequencing. The product pointed out by line c does not comigrate with either the Maxam and Gilbert products or the DNase I products.

$Ce_2(HPTA)$ cleavage results from the 181-bp 3'-end labeled restriction fragment, generated from the treatment of Litmus 29 DNA with BamH I and Pvu II, indicate that the major products comigrate with products from both the Maxam and Gilbert and the DNase I lanes, indicating the presence of 5'-OPO$_3$ products as illustrated in FIG. 4b, lines a and b. There is a minor product band, shown by line c of FIG. 4b, that probably corresponds to 5'-OH reaction products. The presence of both 5'-OPO$_3$ and 3'-OH ends and the lack of reaction products consistent with an oxidative pathway indicates that the Ce$_2$(HPTA)-catalyzed cleavage of DNA uses a hydrolytic mechanism.

The Litmus 29 plasmid DNA, prepared from DH5α cells, and the pBR322 plasmid DNA, prepared from JM109 cells, were both purified using Qiagen Plasmid Maxi Kits. The enzymes Hind III, Pvu II, calf intestinal phosphatase and RQ DNase I were purchased from Promega, BamH I and T4 polynucleotide kinase were purchased from New England Biolabs, and the Klenow fragment of DNA polymerase I was purchased from Gibco BRL. All radioactive nucleotides were ordered from Amersham Life Sciences. The ligand HPTA was purchased from Aldrich. All materials used were molecular biology grade when available, otherwise the purest available material was used. Ce$_2$(HPTA) was prepared in situ using two equivalents of (NH$_4$)$_2$Ce(NO$_3$)$_6$ per HPTA ligand.

5'-end labeled 172-bp restriction fragments were prepared using the following procedure. Litmus 29 plasmid DNA was treated with 50 U of Hind III followed by ethanol precipitation. The DNA was then treated with 3 U of calf intestinal phosphatase followed by heat treatment at 75° C. for 10 minutes in the presence of 10 mM pH 8 EDTA. After phenol:chloroform:isoamyl alcohol treatment and ethanol precipitation the DNA was 5'-end-labled with 2 U T4 polynucleotide kinase in the presence of γ$^{32}$P-ATP. The DNA was then treated with phenol:chloroform:isoamyl alcohol and run through a Sephadex G-50 column equilibrated to pH 8 with Tris buffer. After NH$_4$OAc/ethanol precipitation, the DNA was treated with 4 U of Pvu II and purified with a 6% non-denaturing PAGE gel. The DNA was visualized by exposure to x-ray film and purified from the gel using the crush and soak method.

3'-end labeled 181-bp restriction fragments were prepared using the following procedure. Litmus 29 DNA (2 μg) was treated with 15 U of BamH I at 37° C. followed by phenol:chloroform:isoamyl alcohol extraction and ethanol precipitation. The DNA was then treated with 4 U of the Klenow fragment and γ$^{32}$P-dATP on ice using fill-in conditions, provided by Gibco BRL, and extracted with phenol:chloroform:isoamyl alcohol followed by a Sephadex G-50 spin column and ethanol precipitation. The sample was then treated with 20 U Pvu II at 37° C. and purified on a 6% nondenaturing PAGE gel. The DNA was visualized by exposure to x-ray film and purified from the gel using the crush and soak method.

The 5' and 3'-end-labelled restriction fragments (800,000–1,000,00 cpm) were treated with 0.1 mM Ce$_2$(HPTA) in the presence of 0.25 μg/10 μl corresponding unlabeled restriction fragments of Litmus 29 in 10 mM Tris pH 8.0 in a total volume of 100 μl. All reactions were done in triplicate. After seven hours of incubation at 55° C. in a covered heating block, the samples were ethanol precipitated and resuspended in 20 μl H$_2$O. Dephosphorylation of the 3'-ends of the 5'-end labelled 172 bp DNA fragment was carried out by treating half of a reaction sample (10 μl) with 25 U of T4 polynucleotide kinase in a 50 μl volume at 37° C. followed by ethanol precipitation and resuspension in formamid dye buffer. Dephosphorylation of the 5'-ends of the 3'-end-labelled 181-bp DNA fragment was carried out by treating half a reaction sample (10 μl) with 2.5 U of calf intestinal phosphatase in a 50 μl volume at 37° C. followed by phenol:chloroforin:isoamyl alcohol extraction and ethanol precipitation and resuspension in formadid dye buffer. Maxam Gilbert reactions followed standard molecular biology protocols (*Sambrook Molecular Cloning: A Laboratory Manual,* Cold Spring Harbor Laboratory Press, 1989). DNase reactions were carried out in 10 mM Tris for 15 minutes with serial dilutions of DNase I. The samples were run on a 20% denaturing PAGE 7 M urea gel for 210 minutes at 50 watts, then exposed to Fuji RX x-ray film.

All patents, patent documents, and publications cited above are incorporated herein by reference. The foregoing detailed description has been given for clarity of understanding only and no unnecessary limitations are to be understood therefrom. The invention is not limited to the exact details shown and described, for obvious modifications will occur to those skilled in the art.

What is claimed is:

1. An in vitro method for cleaving a nucleotide sequence comprising contacting the nucleotide sequence to be cleaved with a cationic dinuclear metal complex with one or two polydentate ligands to cleave the nucleotide sequence in its phosphate backbone to form a hydroxyl end and a phosphate end, wherein the polydentate ligand is tethered to a nucleotide sequence recognition element.

2. The method of claim 1 which is carried out in the presence of a dioxygen source.

3. The method of claim 2 wherein the dioxygen source is $O_2$.

4. The method of claim 1 wherein the cationic dinuclear metal complex is a dinuclear metal complex with one ligand containing two tridentate chelating groups linked by a polyatomic chain.

5. The method of claim 1 wherein the nucleotide sequence to be cleaved is a DNA sequence.

6. The method of claim 5 wherein the nucleotide sequence to be cleaved is double stranded, and wherein the cleavage is double-stranded cleavage effective to form linear DNA.

7. The method of claim 1 wherein the nucleotide sequence to be cleaved is an RNA sequence.

8. The method of claim 7 wherein the nucleotide sequence to be cleaved is double stranded.

9. The method of claim 1 wherein the metal complex is a complex of a Lewis acidic metal.

10. The method of claim 9 wherein the metal is a Group IIIA, IB, VB, VIIB, VIIIB, or lanthanide metal.

11. The method of claim 10 wherein the metal is a Group IIIA, VIIIB, or a lanthanide series metal.

12. The method of claim 11 wherein the metal is a lanthanide metal.

13. The method of claim 1 wherein the ligand is represented by the formula $(R^1)(R^2)N$—$R^3$—$N(R^4)(R^5)$ wherein:
  (a) each of $R^1$, $R^2$, $R^4$, and $R^5$ is independently a Lewis basic group; and
  (b) $R^3$ is a substituted or unsubstituted aromatic or aliphatic group with at least a 3 carbon chain.

14. The method of claim 13 wherein $R^3$ is selected from the group consisting of —$CH_2$—$CH(OH)$—$CH_2$—, —$CH_2CH_2$—$CH(OH)$—$CH_2CH_2$—, and —$CH_2$—$CH(OH)$—$CH_2CH_2$—.

15. The method of claim 14 wherein $R^3$ is —$CH_2$—$CH(OH)$—$CH_2$—.

16. The method of claim 13 wherein each of $R^1$, $R^2$, $R^4$, and $R^5$ includes a carboxyl group.

17. The method of claim 13 wherein the metal is a lanthanide metal.

18. An in vitro method for cleaving a nucleotide sequence comprising contacting the nucleotide sequence to be cleaved with a cationic dinuclear metal complex selected from the group of $Fe_2(HPTB)(OH)(NO_3)_4$, $Fe_2(HPTP)(OH)(NO_3)_4$, and $[Fe_2(HPTP)(OBz)](BPh_4)_2$, wherein HPTB and HPTP are tethered to a nucleotide sequence recognition element.

19. An in vitro method for cleaving a supercoiled double-stranded DNA sequence comprising contacting the supercoiled double-stranded DNA sequence to be cleaved with a cationic dinuclear metal complex with one or two polydentate ligands to cleave the nucleotide sequence in its phosphate backbone to form a hydroxyl and a phosphate end on each original DNA strand, wherein the polydentate ligand is tethered to a nucleotide sequence recognition element.

20. The method of claim 19 which is carried out in the presence of a dioxygen source.

21. The method of claim 20 wherein the dioxygen source is $H_2O_2$, or $O_2$ in the presence of a reductant.

22. The method of claim 19 wherein the metal complex is a complex of a Group IIIA, IB, VB, VIIB, VIIIB, or a lanthanide series metal.

23. The method of claim 22 wherein the metal complex is a complex of a lanthanide series metal.

24. The method of claim 19 wherein the polydentate ligand is represented by the formula $(R^1)(R^2)N$—$R^3$—$N(R^4)(R^5)$ wherein:
  (a) each of $R^1$, $R^2$, $R^4$, and $R^5$ is independently a Lewis basic group; and
  (b) $R^3$ is a substituted or unsubstituted aromatic or aliphatic group with at least a 3 carbon chain.

25. The method of claim 19 wherein $R^3$ is selected from the group consisting of —$CH_2$—$CH(OH)$—$CH_2$—, —$CH_2CH_2$—$CH(OH)$—$CH_2CH_2$—, and —$CH_2$—$CH(OH)$—$CH_2CH_2$—, and each of $R^1$, $R^2$, $R^4$, and $R^5$ includes a carboxyl group.

26. An in vitro method for cleaving a nucleotide sequence comprising contacting the nucleotide sequence to be cleaved with a cationic dinuclear metal complex with one or two ligands, each containing two tridentate chelating groups linked by a polyatomic chain, to cleave the nucleotide sequence in its phosphate backbone to form a hydroxyl and a phosphate end; wherein:
  (a) the metal complex includes a metal selected from a group consisting of a Group IIIA, IB, VB, VIIB, VIIIB, or a lanthanide series metal; and
  (b) the ligand is represented by the formula $(R^1)(R^2)N$—$R^3$—$N(R^4)(R^5)$ wherein:
    (I) each of $R^1$, $R^2$, $R^4$, and $R^5$ is independently a Lewis basic group; and
    (ii) $R^3$ is a substituted or unsubstituted aromatic or aliphatic group with at least a 3 carbon chain; and
  wherein the polydentate ligand is tethered to a nucleotide sequence recognition element.

27. The method of claim 26 which is carried out in the presence of a dioxygen source.

28. The method of claim 26 wherein the nucleotide sequence is a double-stranded supercoiled DNA sequence.

* * * * *

UNITED STATES PATENT AND TRADEMARK OFFICE
CERTIFICATE OF CORRECTION

PATENT NO. : 6,143,879
DATED : November 7, 2000
INVENTOR(S) : Que, Jr. et al.

It is certified that error appears in the above-identified patent and that said Letters Patent is hereby corrected as shown below:

Title page,
Column 1, under [56] References, OTHER PUBLICATIONS, in the "Francois et al. (I)" citation, delete "Francois et al. (I)" and replace with -- Francois et al. --.

Title page,
Column 1, under [56] References, OTHER PUBLICATIONS, in the above-mentioned "Francois et al." citation, delete "Nuclëases Artificielles: Coupures Spëcifiques de la Double Hëlice d'ADN par des Oligonuclëotides liës au Complexe Cuivre-Phënanthroline" and replace with -- Nucléases Artificielles: Coupures SpécifIques de la Double Hélice d'ADN par des Oligonucléotides liés au Complexe Cuivre-Phénanthroline --.

Title page,
Column 1, under [56] References, OTHER PUBLICATIONS, in the "Francois et al. (II" citation, delete "Francois et al. (II" and replace with -- Francois et al. --.

Title page,
Column 1, under [56] References, OTHER PUBLICATIONS, in the " Hëlëne et al." citation, delete "Hëlëne et al." and replace with -- Héléne et al. --.

Title page,
Column 2, under [56] References, OTHER PUBLICATIONS, in the "Sun et al." citation, delete "Oligo-α-thymidylate-Phenanthorline" and replace with -- Oligo-α-thymidylate-Phenanthroline --.

Title page,
Column 2, under [56] References, OTHER PUBLICATIONS, in the "Biodet-Forget et al." citation, delete "SIngle-Stranded and Double-Stranded DNA Serquences" and replace with -- Single-Stranded and Double-Stranded DNA Sequences --.

Title page,
Column 2, under [56] References, OTHER PUBLICATIONS, in the "Hëlëne et al." citation, delete "Hëlëne et al." and replace with -- Héléne et al. --.

Title page,
Column 4, under [56] References, OTHER PUBLICATIONS, in the "Modak et al." citation, delete "(Iss. No." and replace with -- (Iss. No. 1) --.

UNITED STATES PATENT AND TRADEMARK OFFICE
CERTIFICATE OF CORRECTION

PATENT NO. : 6,143,879
DATED : November 7, 2000
INVENTOR(S) : Que, Jr. et al.

It is certified that error appears in the above-identified patent and that said Letters Patent is hereby corrected as shown below:

Title page,
Column 4, under [56] References, OTHER PUBLICATIONS, in the "Pyle et al., 'Shape-Selective Targeting of DNA by (Phenanthrenequinone diimine) rhodium (III) Photocleaving Agents,'" citation, delete "(Iss. No 1" and replace with -- (Iss. No. 12) --.

Title page,
Column 5, under [56] References, OTHER PUBLICATIONS in the "Sugiyama et al, 'Chemistry of the Alkali-Labile Lesion Formed for Iron (II) Bleomycin and d (CGCTTTAAAGCG),'" delete "for" and replace with -- from --.

Signed and Sealed this

Second Day of October, 2001

Attest:

NICHOLAS P. GODICI
Attesting Officer
Acting Director of the United States Patent and Trademark Office